United States Patent [19]

Hay

[11] 4,064,179
[45] Dec. 20, 1977

[54] ORGANOMERCAPTOPHENOL

[75] Inventor: Allan S. Hay, Schenectady, N.Y.

[73] Assignee: General Electric Company, Schenectady, N.Y.

[21] Appl. No.: 649,708

[22] Filed: Jan. 16, 1976

Related U.S. Application Data

[62] Division of Ser. No. 484,986, July 1, 1974, Pat. No. 3,952,063.

[51] Int. Cl.² ............................................ C07C 149/36
[52] U.S. Cl. ..................... 260/609 F; 260/453 AR; 260/463; 260/619 R; 260/624 R; 252/404; 252/406
[58] Field of Search ..................................... 260/609 F

[56] References Cited

U.S. PATENT DOCUMENTS 3,939,210  2/1976  Bajer ................................. 260/609 F Primary Examiner—Lewis Gotts
Assistant Examiner—Molly C. Eakin
Attorney, Agent, or Firm—F. Wesley Turner; Joseph T. Cohen; Jerome C. Squillaro

[57] ABSTRACT

A novel organomercaptophenol is described.

5 Claims, No Drawings

ORGANOMERCAPTOPHENOL

This is a division, of application Ser. No. 484,986, filed July 1, 1974, now U.S. Pat. No. 3,952,063.

This invention relates to a process for the preparation of an organo-mercapto-phenol under reaction conditions which comprise contacting sulfur and a phenol in the presence of (1) a base, and (2) an activated olefin or an epoxy compound. In a preferred embodiment, the process is carried out in the presence of catalytic amounts of an alkali metal base.

Various observations have been made by the prior art regarding reactions between phenolic reactants and sulfur carried out in the presence of a base, such as those described in:

I. A. J. Neale's description of the preparation of monothiobisphenols and oligomeric phenols by the reaction of phenol and sulfur at temperatures of 140°-180° C. during time periods of 6 to 24 hours (Tetrahedron, Vol. 25, Pergamon Press (1969). Printed in Great Britain, pages 4593 to 4597);

II. E. J. Geering's description of the preparation of a phenol-sulfide having an average of at least two sulfur atoms per linkage by the reaction sulfur and a phenolic reactant having at least one ortho position substituted by hydrogen at temperatures of 100–200° C. during time periods of ½ to 15 hours (A. J. Geering, et al., U.S. Pat. No. 3,647,885);

III. T. Fujisawa's description of the preparation of 4-arylthio-2,6-dialkylphenols by the reaction of 2,6-dialkylphenols and aromatic disulfides carried out at elevated temperatures during time periods of ½ to 50 hours in the presence of a solvent (Fujisawa et al., U.S. Pat. No. 3,697,601, further described by Fujisawa in the article *Sulfenylation of Hindered Phenols With Aryl Disulfides*, J. Org. Chem., Vol. 38, No. 4 (1973) Pages 687–690);

IV. T. Fujisawa, K. Hata, and T. Kojima's description of the perparation of thiobis-2,6-dialkylphenols and polythiobis-2,6-dialkylphenols by the reaction of 2,6-disubstituted sterically hindered phenols with sulfur in an alcohol at room temperatures to 100° C. during time periods of ½ 1 hour (Synthesis, Vol. 1, January 1973, pages 38–39).

Other prior art publications, among others, which relate to the reaction of phenol and sulfur which illustrate the state of the art are the following:

E. J. Geering et al., U.S. Pat. Nos. 3,717,682 and 3,743,680, as well as *Rearrangements and Decompositions of Thiobisphenols* by A. J. Neale et al., Tetrahedron, Vol. 25, Pergamon Press (1969) Printed in Great Britain, pages 4593–4597.

Essentially, this invention embodies a process for the preparation of an organomercaptophenol which comprises contacting sulfur and a phenol carried out in the presence of (1) a base, and (2) an olefin or an epoxy compound. In a preferred embodiment, the process is carried out in the presence of catalytic amounts of base.

The process of preparing an organomercaptophenol comprises the reaction of any phenol having at least one hydrogen atom in the ortho position relative to the position of the hydroxyl group of the phenol subject to the proviso that any other substituents do not interfere with the formation of an organomercaptophenol in accordance with the reaction parameters of this invention. Among others, phenols suited to the practice of this invention can be described by the following structural formula:

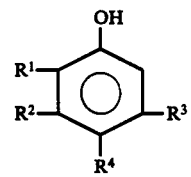

I.

wherein independently each $R^1$, $R^2$, $R^3$ and $R^4$ is a monovalent substituent selected from the group consisting of hydrogen, hydrocarbon and hydrocarbonoxy radicals. Preferably the hydrocarbon and hydrocarbonoxy radicals have from 1 to 30, more preferably from 1 to 15, and even more preferably from 1 to 6 carbon atoms. Representative of phenols of Formula I., among others, which can be employed are as follows:

phenol (also known as hydroxybenzene)
2-methylphenol (ortho-cresol),
3-methylphenol (meta-cresol),
4-methylphenol (para-cresol),
2,3-dimethylphenol,
2,4,5-trimethylphenol,
2-ethylphenol,
2,4-dimethylphenol,
3,5-dimethylphenol (3,5-xylenol),
the 2-propylphenols (2-n-propyl and 2-sec-propylphenol),
2,4-dipropylphenols (2,4-di-n-propyl and 2,6-di-sec-propylhenol),
the 3,5-dipropylphenols (3,5-di-n-propyl and 3,5-di-sec-propylphenol),
2-n-butylphenol,
2-sec-butylphenol-2,4-di-tert-butylphenol,
the 2,4-dibutylphenols (2,4-di-n-butyl, 2,4-di-sec-butyl, and 2,4-di-tert-butylphenol),
2-cyclohexylphenol,
the 2,4-dioctylphenols,
the 3,5-dioctylphenols,
the 2,3-didodecylphenols,
the 2-tridecylphenols,
the 2,4-ditridecylphenols,
the 3,5-ditetradecylphenols,
the 2-octadecylphenols,
the 2,4-didocosylphenols,
the 2,4-dihexacosylphenols,
the 3,5-ditriacontylphenols,
2-phenylphenol,
2,4-diphenylphenol,
3,5-diphenylphenol,
2-benzylphenol,
2,4-dibenzylphenol,
4,5-dibenzylphenol,
the 3,5-ditolylphenols,
2-naphthylphenol,
the 2,4-dinaphthylphenols,
2-methoxyphenol,
4-methoxyphenol,
2,4-dimethoxyphenol,
2,5-dimethoxyphenol,
3,5-dimethoxyphenol,
4-ethoxyphenol,
2-ethoxy-4-methoxyphenol,
3,5-diethoxyphenol,
2-butoxyphenol,
2,4-dilauroxyphenol,
2-phenoxyphenol, 2,4-diphenoxyphenol,
3,5-diphenoxyphenol,
2-naphthoxyphenol,
2,4-dibenzyloxyphenol,
3-methyl-5-tert-butylphenol,
the 2-propyl-6-phenylphenols, etc.

The hydrocarbon and hydrocarbonoxy substituents of Formula I can be the same or different and can be selected from the group consisting of alkyl, cycloalkyl, aryl, alkoxy, cycloalkoxy, aryloxy, and combinations thereof. A preferred phenol reactant class within the practice of this invention are the phenols having $R^1$, $R^2$, $R^3$ and $R^4$ substituents selected from hydrogen and the lower alkyl group consisting of $C_{1-2}$ radicals. Particularly preferred is phenol and the isomeric methylphenols.

My process employs sulfur in any of its elemental forms or as polysulfide ions represented by the generic formula $M_yS_x$ wherein $x$ is a positive integer at least equal to 2 and wherein M is selected from the group consisting of alkali and alkaline earth metals as well as ammonium ions $R_4N^+$ where R is hydrogen or a hydrocarbon. Preferably elemental sulfur is employed. Because of its economic advantage, elemental sulfur can be employed in any of the commonly known commercial forms, such as bright sulfur (99.5%), dark sulfur (up to 1% carbonaceous material), refined sulfur (99.8%); high purity sulfur (99.97%); sublimed sulfur (flowers of sulfur); flour sulfur, ground refined or crude sulfur in various mesh sizes; and Rubbermakers, a ground special grade.

Any base that can be employed which will dissolve in the phenol reaction mixture and form a metal phenoxide (sometimes referred to as a metal phenolate or phenates). Representative among others, of basic species which can be employed are elemental alkali and alkaline earth metals; ammonium alkali or alkaline earth metal hydroxides; salts of strong bases and weak organic acids; etc. Specific examples include sodium, potassium and magnesium metal; ammonium sodium, potassium, lithium, and calcium hydroxide; ammonium sodium, lithium, and barium carbonates, sodium acetate, sodium benzoate, sodium methylate, sodium thiosulfate, sodium sulfide, sodium tetrasulfide, sodium cyanate, etc. Preferred basic species are the metals sodium and potassium, sodium and potassium hydroxides and salts of sodium and potassium bases and weak organic acids.

In accordance with the process of this invention, in addition to the phenol, sulfur and base, the process is carried out in the presence of a promoter which shifts the equilibrium point of the reaction in favor of the formation of the organomercaptophenol. These promoters are selected from the class consisting of activated olefins and epoxy compounds. Among others, activated olefin compounds may be represented by the Formula II set out hereafter:

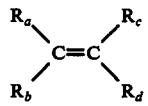

II.

wherein independently at least one of the $R_a$, $R_b$, $R_c$ and $R_d$ substituents is selected from the electron-attracting group consisting of cyano, i.e., —CN; carbamoyl, i.e., —CON(R')$_2$; oxycarbonyl, i.e., —COOR''; oxohydrocarbyl, i.e., —COR'', radicals; wherein independently each R' represents hydrogen, acyclic and cyclic hydrocarbon radicals, independently R'' represents acyclic and cyclic hydrocarbon radicals.

Preferably the activated olefins have from 3 to 10 carbon atoms, more preferably from 3 to 5 carbon atoms. The olefins may be either mono-or polyolefinic and may be either conjugated or non-conjugated in unsaturation. Among others, representative of activated olefin species are such compounds as acrylamide, α-methylacrylamide, N-methylacrylamide, N-phenylacrylamide, N,N-diisobutylacrylamide, α-acrylonitrile, α-phenylacrylonitrile, vinyl chloride, vinylidene chloride, vinyl methyl ether, vinyl ethyl ether, vinyl n-propyl ether, vinyl n-octyl ether, vinyl n-octadecyl ether, vinylidenecyanide, sometimes referred to as methylene malonitrile, vinyl succinimide, N-vinyl N-methylacetamide, N-vinyl N-phenylacetamide, N-vinyl diglycolylimide, etc. Preferred olefins are monoolefinic $C_3$–$C_5$ carbonitrides, such as acrylonitrile, α-methyl acrylonitrile, α-ethyl acrylonitrile, butyronitrile and α-methylbutyronitrile.

Among others, epoxy compounds can be represented by the Formula III set out hereafter:

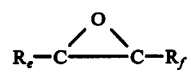

III.

wherein independently each $R_e$ and $R_f$ substituents are selected from the group consisting of hydrogen, acyclic and cyclic radicals. Preferably, the $R_e$ and $R_f$ radicals are free of any electron-attracting substituents which can substantially reduce the ease of carbon-oxygen bond breakage. Preferred epoxy compounds are epoxides containing from 2 to 10 carbon atoms, more preferably from 2 to 5 carbon atoms. The epoxides may be mono- or polyepoxy compounds, i.e., compounds which contain more than one reactive epoxy group. Among others, representative of epoxy compounds are such compounds as ethylene oxide, propylene oxide, 2,3-epoxybutane, 1,2-butyleneoxide, also known as 1,2-epoxybutane, trimethylethylene oxide, tetramethylethylene oxide, butadiene monoxide, styrene oxide, α-methylstyrene oxide, 1,1-diphenylethylene oxide, hexyl glycidyl ether, allyl glycidyl ether, phenyl glycidyl ether, o-chlorophenyl glycidyl ether, methacrylyl chloride epoxide, glycidyl methacrylate, 1,2-epoxy-4-vinylcyclohexane, 2,3-epoxyoctane; 4-butylphenyl glycidyl ether, dipentene monoxide, α-pinene oxide, etc. Preferred epoxides are $C_2$–$C_5$ monoepoxides, such as ethyleneoxide, propyleneoxide, 1,2-butyleneoxide and trimethylethyleneoxide.

In general, the process can be carried out in the absence of any solvent, e.g. where the phenol acts as both a reactant and as a solvent, or in the presence of any solvent which forms a solution in combination with phenol, sulfur, base and the promoter. In general, in the process of this invention, it is desirable that the solvent employed be selected from a group consisting of any nonpolar or polar solvent subject to the proviso that the solvent employed be substantially free of high dielectric constant solvents i.e. solvents incapable of strong hydrogen bonding to the phenol reactant or any intermediates derived therefrom during the course of the reaction. In general, solvents which are preferably excluded are solvents commonly referred to as polar aprotic solvents which solvents are characterized as solvent species which do not have the capability of donating strong hydrogen bonding to solute species and which have high dielectric constants, e.g. dielectric constants of from about 20 to about 50, or even higher.

Among others, suitable solvents in the process of this invention that can be employed are the following:

A. non- or low-polar solvents such as hexane, 3-methylpentane, heptane, cyclohexane, methylcyclohexane, cyclohexane, isooctane, p-cymene, cumene, decalin, toluene, benzene, diethylether, diphenyl ether, dioxane, thiophene, dimethylsulfide, ethyl acetate, tetrahydrofuran, etc. and mixtures thereof; and B. medium-polar solvents such as chlorobenzene, anisol, bromobenzene, t-butanol, ethanol, methanol, o-dichlorobenzene, methyl formate, iodobenzene, acetone, acetophenone, etc. and mixtures thereof.

In a preferred embodiment of this invention, it is preferred that the reaction be carried out in the presence of a non- or low polar solvent as defined hereinbefore which is characterized in accordance with solvent polarity scales described in the publication *Solute-Solvent Interactions*, J. F. Kotese and K. D. Richey (1969) Marcel Dekker, pages 281–282.

Although not wishing the process of this invention or the scope thereof to be limited by any theory, it is believed that both the rate constants and equilibrium constants associated with the process of this invention are related to (1) the promoter employed, and wherein a solvent other than phenol is employed, to (2) the polarity and the dielectric strength of the solvent employed in the preparation of organomercaptophenol. It is also believed that a proton-transfer reaction is involved which transfer rate and equilibrium constant is significantly affected by the the solvent both in its initial and transition state.

In general, as stated hereinbefore, the process of this invention can be carried out under reaction parameters which broadly comprise contacting a phenol, sulfur, an activated olefin or an epoxy compound, in the presence of a base.

The phenol:sulfur mole ratio can vary widely, however, because minimum theoretical stoichiometry requires the reaction of approximately one gram atom of sulfur reacts with one mole of phenol in the preparation of an organomercaptophenol, a minimum mole:gram atom ratio preferably employed is one mole of phenol to one gram atom of sulfur. The reaction can be carried out at any phenol:sulfur ratio such as ratios within the range of from about 1:0.05 to about 1:20, however, preferably ratios within the range of from about 1:0.5 to about 1:5 and more preferably from about 1:1 to about 1:2 are employed.

Any mole ratio of phenol to base can be employed and can be varied widely. In general, suitable ratios include the use of base in catalytic amounts, e.g. wherein the phenol:base mole ratios are as low as 1:0.001 (0.1 mole % based on phenol) as well as noncatalytic amounts, e.g. wherein the phenol:base mole ratios are as high as 1:5 (500 mole % base based on phenol) or even higher. In general, satisfactory phenol:base proportions are within the range of from about 1:0.01 to about 1:2, more preferably from about 1:0.02 to about 1:1.5 and even more preferably from about 1:0.1 to about 1:1.2.

The amount of activated olefin or epoxy compound (hereinafter occasionally referred to as thioadditives) which is employed can be varied over a wide range. In general, suitable phenol to thioadditive mole ratios are within the range of from about 1:0.01 to about 1:100, more preferably from about 1:0.5 to about 1:5 and even more preferably from about 1:2 to about 1:4. In order to reduce the opportunity of olefin or epoxy O-alkylation of the hydroxy group of the reactant phenol or resulting organomercaptophenol reaction product preferably the phenol:thioadditive mole proportions are restricted to mole ratios no greater than about 1:3. In a preferred embodiment, it is preferred that the thioadditive be added to the reaction medium in a programmed manner, i.e. in a manner in which continuously regulates the amount of thioadditive admitted to the reaction medium in order to insure that the equilibrium and rate constants of the reaction favor the formation of the organomercaptophenols rather than the O-alkylation of phenol or organomercaptophenols.

In general, any reaction temperature can be employed wherein the thermal reaction kinetics are not deleterious as to reaction rates, reaction time, yield and/or conversion of the phenol to the desired organomercaptophenol. In general, the reaction temperatures can be varied widely, however, often fall within the range of from about 0° C. to about 200° C., and more often fall within the temperature range of from about 80° C. to about 120° C. The reaction periods also vary widely, however, generally falling within the range of from about ½ hour to about 5 hours. The process is preferentially carried out in the presence of an inert atmosphere of nitrogen in order to exclude from the reaction medium any oxygen or oxidizing agents which are well-known to oxidize organic sulfides to sulfoxides or sulfones among other undersirable reaction products.

The amount of solvent when employed in accordance with a preferred embodiment of this invention can be any amount and can vary widely. In general, the solvent to phenol ratio can be within the range of from about 1000:1 to about 0.1:1 preferably from about 100:1 to about 2:1 and even more preferably from about 10:1 to about 5:1. The economic effect of any solvent or solvent mixtures employed on the yield of any major end product, i.e., the organomercaptophenols, as opposed to any other minor end product obtained by the practice of this invention can be readily determined by those skilled in the art by means of simple experimentation.

By the practice of this invention, as described hereinbefore organomercaptophenols and O-alkylated organomercaptophenols are prepared having the following structural formula:

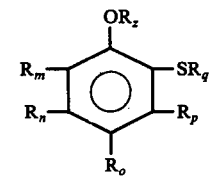

IV.

wherein independently each $R_m$, $R_n$, $R_o$ and $R_p$ is a monovalent substituent selected from the group consisting of hydrogen, hydrocarbon and hydrocarbonoxy radicals, $R_q$ is selected from cyano, carbamoyl, oxycarbonyl, oxyhydrocarbyl and hydroxy substituted monovalent acyclic anc cyclic hydrocarbon radicals, and $R_z$ is a monovalent substituent selected from the group consisting of hydrogen, and cyano, carbamoyl, oxycarbonyl, oxyhydrocarbyl and hydroxy substituted monovalent acyclic and cyclic hydrocarbon radicals.

Preferably, wherein $R_m$, $R_n$, $R_o$, $R_p$ are other than hydrogen, the radicals contain from 1 to 30, more preferably from 1 to 15, and even more preferably from 1 to 6 carbon atoms. Preferably the $R_q$ radical contains from 2 to 30, more preferably from 2 to 15, and even more preferably from 2 to 6 carbon atoms. The hydrocarbon and hydrocarbonoxy substituents of IV can be the same or different and can be selected from the group consisting of alkyl, cycloalkyl, aryl, alkoxy, cycloalkoxy, aryloxy and combinations thereof.

In order that those skilled in the art may better understand my invention, the following examples are given which are illustrative of the best mode of this invention, however, these examples are not intended to limit the invention in any manner whatsoever. In all of the examples, all parts are by weight unless otherwise stated and the following general procedure was employed. For purposes of brevity, only deviations from this procedure will be set out in the examples.

GENERAL PROCEDURE

A solution of phenol, e.g. o-cresol, is charged to a reaction vessel. Base, sodium metal, is added to the phenol solvent mixture and heated to elevated temperatures, e.g. about 100° C. until dissolved. The mixture is cooled, e.g. to a temperature of about 70°–80° C. and sulfur, e.g. elemental sulfur (flowers of sulfur) is added to the reaction mixture. The mixture is heated to elevated temperatures, e.g. about 100° C., and the promoter is added over a 2–4 hour period. The resulting reaction mixture, generally, is not homogeneous and vigorous stirring is required. The mixture is cooled and diluted if necessary with a suitable diluent, e.g. ether and washed with dilute hydrochloric acid and then with water and dried with a suitable drying agent, e.g. $MgSO_4$. The resulting product is washed after removal of the solvent and is purified by distillation or by recrystallization from a suitable solvent, e.g. acetic acid. The organomercaptophenol recovered is characterized by its melting point in both its crude and purified form, and analytically characterized, based upon a correlation between calculated and found carbon, hydrogen, oxygen, sulfur of the organomercaptophenol.

If the product desired is the o-alkylate of the organomercaptophenol with one mole of promoter, the reaction mixture after cooling and dilution with a suitable solvent, e.g. ether, is washed with dilute sodium hydroxide to separate any phenolic materials and the residue after drying and removing solvent is distilled to yield pure product.

TABLE I

Summary of Experimental Data - Run Nos. 1–11

| Run No. | Reaction Products Composition | Yield | Reactants(R), Base(B), Solvent(S), Promoter(P) | | Conv. | Temp. | Time | Mole Ratios Phenol:Sulfur: Base:Promoter |
|---|---|---|---|---|---|---|---|---|
| 1. (a) | 2-(2-hydroxypropylthio)phenol Analysis:calc.:58,69C,6.57H, 17.38S found:58.6C,6.5H,17.5S | 25% | (R) phenol, sulfur, (B) sodium metal, (S) — | 94.1g(1.0m) 32.1g(1.0m) 1.2g(0.05m) | 65% | 155° C | 1.5hrs | 1:1:0.05:1 |
| (b) | 2-hydroxypropoxybenzene | 13% | (P) propylene oxide, | 58.1g(1.0m) | | | | |
| (c) | 1-(2-hydroxypropoxy)-2-(2-hydroxypropylthio)benzene | 8% | | | | | | |
| 2. (a) | 2-hydroxypropoxybenzene Analysis:calc.:59.49C,7.49N, 13.21S found:59.9C,7.6H,13.6S | 41% | (R) phenol, sulfur, (B) sodium metal, (S) — | 94.1g(1.0m) 48.1g(1.5m) 2.9g(0.125m) | 100% | 130° C | 6 hrs | 1:1.5:0.125:3 |
| (b) | 1-(2-hydroxypropoxy)-2-(2-hydroxypropylthio)benzene | 29% | (P) propylene oxide, | 166.1g(2.9m) | | | | |
| (c) | 2,2'-di(2-hydroxypropoxy)-diphenyl sulfide and isomers, (i) 2,4'-di(2-hydroxypropoxy)-diphenyl sulfide (ii) 4,4'-di(2-hydroxypropoxy)-diphenyl sulfide | 7% | | | | | | |
| 3. (a) | 2-(2-hydroxypropylthio)phenol | 23% | (R) phenol, sulfur, (B) sodium metal, (S) — (P) propylene oxide, | 94.1g(1.0m) 32.6g(1.0m) 1.2g(0.05m) 58.1g(1.0m) | 52% | 130° C | 2 hrs | 1:1:0.05:1 |
| (b) | 1-(2-hydroxypropoxy)-2-(2-hydroxypropylthio)benzene | 1% | | | | | | |
| 4. (a) | 1-(2-hydroxypropoxy)-2-(2-hydroxypropylthio)benzene | 17% | (R) phenol, sulfur, (B) sodium metal (S) — (P) propylene oxide, | 94.1g(1.0m) 32.1g(1.0m) 2.88g(0.125m) 106.2g(1.8m) | 100% | 130° C | 5 hrs | 1:1:0.125:2 |
| (b) | 2,2'-di(2-hydroxypropoxy)-diphenyl sulfide | 7% | | | | | | |
| 5. (a) | 1-hydroxyethoxybenzene | 22% | (R) phenol, sulfur, (B) sodium metal, (S) — (P) ethylene oxide, | 94.1g(1.0m) 48.0g(1.5m) 2.88g(0.125m) in excess g | 100% | 130° C | 6 hrs | 1:1.5:0.125: |
| (b) | 1-(1-hydroxyethoxy)-2-(1-hydroxyethylthio)benzene Analysis:calc.:56.07C,6.59H, 14.94S found:55.9C,6.6H,15.2S | 14% | | | | | | |
| (c) | 2,2'-di(1-hydroxyethoxy)-diphenyl sulfide | 1% | | | | | | |
| 6. (a) | 2-methyl-6-(2-hydroxypropylthio)phenol Analysis:calc.:60.59C,7.12H, 16.15S found:60.4C,7.2H,16.5S | 56% | (R) o-cresol, sulfur, (B) sodium metal, (S) — (P) propylene oxide, | 108.1g(1.0m) 32.1g(1.0m) 1.2g(0.05m) 58.1g(1.0m) | 59% | 130° C | 1.5hrs | 1:1:0.05:1 |
| (b) | di(2-hydroxypropyl)disulfide | 26%, (23.7g) | | | | | | |
| (c) | 1-methyl-2-(2-hydroxypropoxy)-3-(2-hydroxypropylthio)-benzene | 1% | | | | | | |
| 7. (a) | 1-methyl-2-(2-hydroxypropoxy)-3-(2-hydroxypropylthio)-benzene Analysis:calc.:60.92C,78.87H 12.48S found:61.4C,7.7H,13.0S | 32% | (R) o-cresol, sulfur, (B) sodium metal (S) — (P) propylene oxide, | 108.1g(1.0m) 48.0g(1.5m) 1.2g(0.05m) 159.1g(2.74m) | 98% | 130° C | 7 hrs | 1:1.5:0.05:2.7 |
| (b) | 1-methyl-2-(2-hydroxypro- | 25%, | | | | | | |

TABLE I-continued
Summary of Experimental Data - Run Nos. 1-11

| Run No. | | Reaction Products Composition | Yield | | Reactants(R), Base(B), Solvent(S), Promoter(P) | | Conv. | Temp. | Time | Mole Ratios Phenol:Sulfur:Base:Promoter |
|---|---|---|---|---|---|---|---|---|---|---|
| | | poxy)benzene | (40.1g) | | | | | | | |
| | (c) | di(2-hydroxypropyl)disulfide | 7.3%, (10.1g) | | | | | | | |
| | (d) | 3,3'-dimethyl-2,2'-(2-hydroxy-propoxy)diphenyl sulfide and isomers | 3%, (5.9g) | | | | | | | |
| 8. | (a) | 1-methyl-2-(2-hydroxypro-poxybenzene | 33% | (R) | o-cresol, sulfur, | 21.6g(0.2m) 6.4g(0.2m) | 60% | 120° C | 4.5hrs | 1:1:0.05:1 |
| | (b) | 1-methyl-2-(2-hydroxypro-poxy)-3-(2-hydroxypropylthio)-benzene | 16% | (B) (S) | sodium hydroxide, N-methylpyrroli-done, toluene, | 0.4g(0.01m) 124ml 80ml | | | | |
| | | | | (P) | propylene oxide, | 11.62g(0.2m) | | | | |
| 9. | (a) | 1-methyl-2-(2-hydroxypro-poxy)benzene | 25%, (41.6g) | (R) | o-cresol, sulfur, | 108.1g(1.0m) 64.1g(2.0m) | 99% | 130° C | 7 hrs | 1:2:0.125:4 |
| | (b) | 1-methyl-2-(2-hydroxypro-poxy)-3-(2-hydroxypropylthio)-benzene | 19% | (B) (S) | sodium metal, — | 2.9g(0.125m) | | | | |
| | (c) | 3,3'-dimethyl-2-,2'-(2-hydroxy-propoxy)diphenyl sulfide | 1% | (P) | propylene oxide, | 232.4g(4.0m) | | | | |
| 10. | (a) | 1-methyl-2-(2-hydroxypro-poxy)-3-(2-hydroxypropylthio)-benzene | 24% | (R) | o-cresol, sulfur, | 108.1g(1.0m) 64.1g(2.0m) | 100% | 130° C | 5 hrs | 1:2:0.05:3 |
| | (b) | 1-methyl-2-(2-hydroxypro-poxy)benzene | u.d. | (B) (S) | potassium cyanide, — | 3.26g(0.05m) | | | | |
| | | | | (P) | propylene oxide, | 184.97g(3.2m) | | | | |
| 11. | (a) | 1-methyl-2-(2-hydroxypro-poxy)-3-(2-hydroxypropylthio)-benzene | 25% | (R) | o-cresol, sulfur, | 108.1g(1.0m) 64.1g(2.0m) | 89% | 130° – 140° C | 7.0 hrs | 1:2:0.05:2.7 |
| | (b) | 1-methyl-2-(2-hydroxypro-poxy)benzene | 11% | (B) (S) | sodium metal, — | 1.2g(0.05m) | | | | |
| | | | | (P) | propylene oxide, | 159.2g(2.7m) | | | | |

The organomercaptophenols produced by this process are useful as monomers in the synthesis of esters, carbonates, ethers, epoxy compounds, among many other chemicals synthesized from monohydric phenols. In addition, the organomercaptophenols are also useful as antioxidants.

Several modifications and variations of the invention have been illustrated in the above examples and elsewhere in the disclosure. Accordingly, other modifications and variations will be readily apparent to those skilled in the art in view of applicant's teaching. It is, therefore, to be understood that changes may be made in the particular embodiments of the invention described herein which changes are within the full intended scope of the invention as defined by the appended claims.

What I claim as new and desire to secure by Letters Patent in the United States is:

1. An organomercaptophenol of the formula:

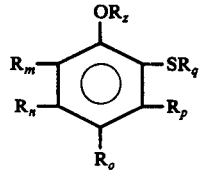

wherein independently each $R_m$, $R_n$, $R_o$ and $R_p$ is hydrogen, or a hydrocarbon or hydrocarbonoxy radical, $R_q$ and $R_z$ are hydroxy substituted monovalent acyclic or cyclic hydrocarbon radicals.

2. The claim 1 organomercaptophenol wherein each $R_m$, $R_n$, $R_o$ and $R_p$ radical contains from 1-30 carbon atoms, and each $R_q$ and $R_z$ radical contains from 2-30 carbon atoms.

3. The claim 2 organomercaptophenol wherein each $R_m$, $R_n$, $R_o$ and $R_p$ radical is alkyl, cycloakyl, aryl, alkoxy, cycloalkoxy, aryloxy or a combination thereof.

4. An organomercaptophenol of the formula:

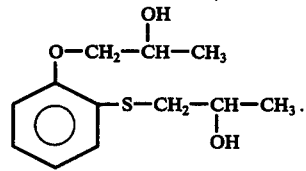

5. An organomercaptophenol of the formula:

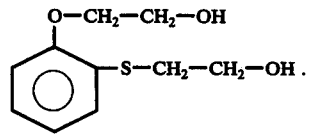

* * * * *